US00PP25921P3

(12) United States Plant Patent

Olesen et al.

(10) Patent No.: US PP25,921 P3

(45) Date of Patent: Sep. 22, 2015

(54) *CLEMATIS* PLANT NAMED 'EVIPO053'

(50) Latin Name: *Clematis viticella*
Varietal Denomination: Evipo053

(71) Applicants: Mogens Nyegaard Olesen, Fredensborg (DK); Raymond J. Evison, St. Sampsons (GB)

(72) Inventors: Mogens Nyegaard Olesen, Fredensborg (DK); Raymond J. Evison, St. Sampsons (GB)

(73) Assignee: POULSEN ROSER A/S, Fredensborg (DK)

( * ) Notice: Subject to any disclaimer, the term of this patent is extended or adjusted under 35 U.S.C. 154(b) by 139 days.

(21) Appl. No.: 13/986,926

(22) Filed: Jun. 14, 2013

(65) Prior Publication Data

US 2014/0373233 P1 Dec. 18, 2014

(51) Int. Cl.
*A01H 5/02* (2006.01)

(52) U.S. Cl.
USPC ..... Plt./228

(58) Field of Classification Search
USPC ..... Plt./228
CPC ..... A01H 5/02; A01H 5/00
See application file for complete search history.

(56) References Cited

PUBLICATIONS

Rice. Gold Medal winners at the National Plant Show posted on Jun. 29, 2010, retrieved on Dec. 15, 2014, retrieved from the Internet at <http://mygarden.rhs.org.uk/blogs/graham_rice/archive/2010/06/29/gold-medal-winners-at-the-national-plant-show.aspx> 2 pp.*

Rice. New Clematis at Hampton Court—Graham Rice's New Plants Blog posted on Jul. 8, 2010, retrieved on Dec. 15, 2014, retrieved from the Internet at <http://mygarden.rhs.org.uk/blogs/graham_rice/archive/2010/07/08/new-clematis-at-hampton-court.aspx> 2 pp.*

* cited by examiner

*Primary Examiner* — June Hwu

(57) ABSTRACT

A new *Clematis* plant with a compact growth habit, profuse, Violet-Blue flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.

Variety denomination: 'Evipo053'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 1999 and the resulting seeds were planted the following winter in a controlled environment in Guernsey, Channel Islands. The new variety named 'Evipo053' originated as a single seedling from the stated cross.

The new *clematis* plant may be distinguished from its female seed parent and male pollen parent primarily by flower color and growth habit.

The objective of the hybridization of this *clematis* plant was to create a new and distinct variety for nursery culture with unique qualities such as:

1. Uniform and abundant Violet-Blue flowers;
2. Vigorous and compact growth, making the variety suitable for container culture;
3. Improved disease resistance; and
4. Flowering from new growth.

This combination of qualities was lacking in *clematis* plants that were in commercial cultivation and the qualities have been substantially achieved in the new variety.

'Evipo053' was selected by Mogens N. Olesen and Raymond J. Evison in their *clematis* development program in the Channel Islands, United Kingdom in 2000. Asexual reproduction of 'Evipo053' by means of vegetative stem cuttings and traditional layering was first performed by Mogens N. Olesen and Raymond J. Evison in the nursery during the summer of 2000. This initial and subsequent asexual propagations have demonstrated that the characteristics of 'Evipo053' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo053'.

Specifically illustrated in FIG. 1 are flowers at various stages of development, undersurface of flower, flower in parts exposing stamens and pistils, juvenile and mature leaves, and stems.

DETAILED DESCRIPTION OF THE VARIETY

Figure 1:
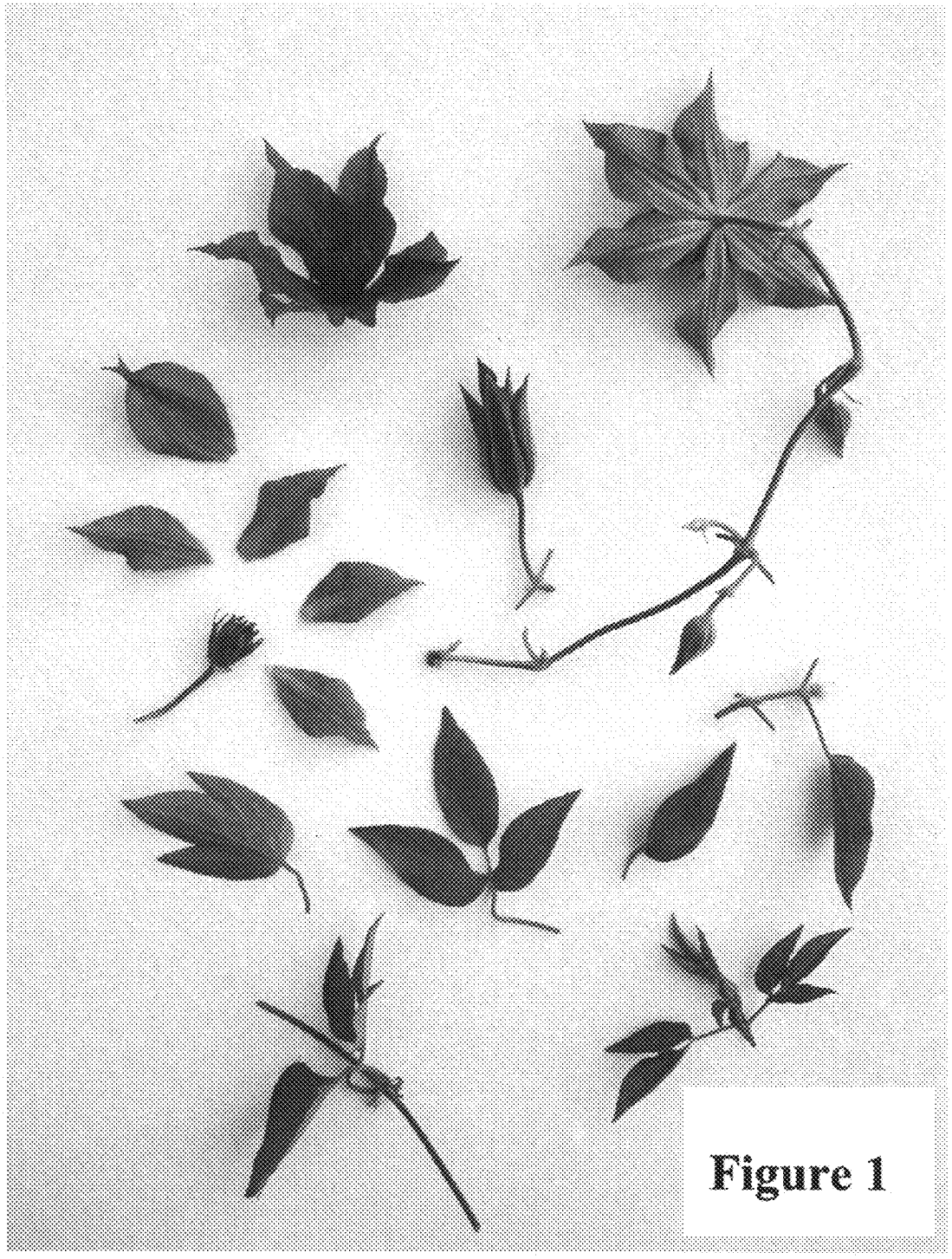
Figure 2:
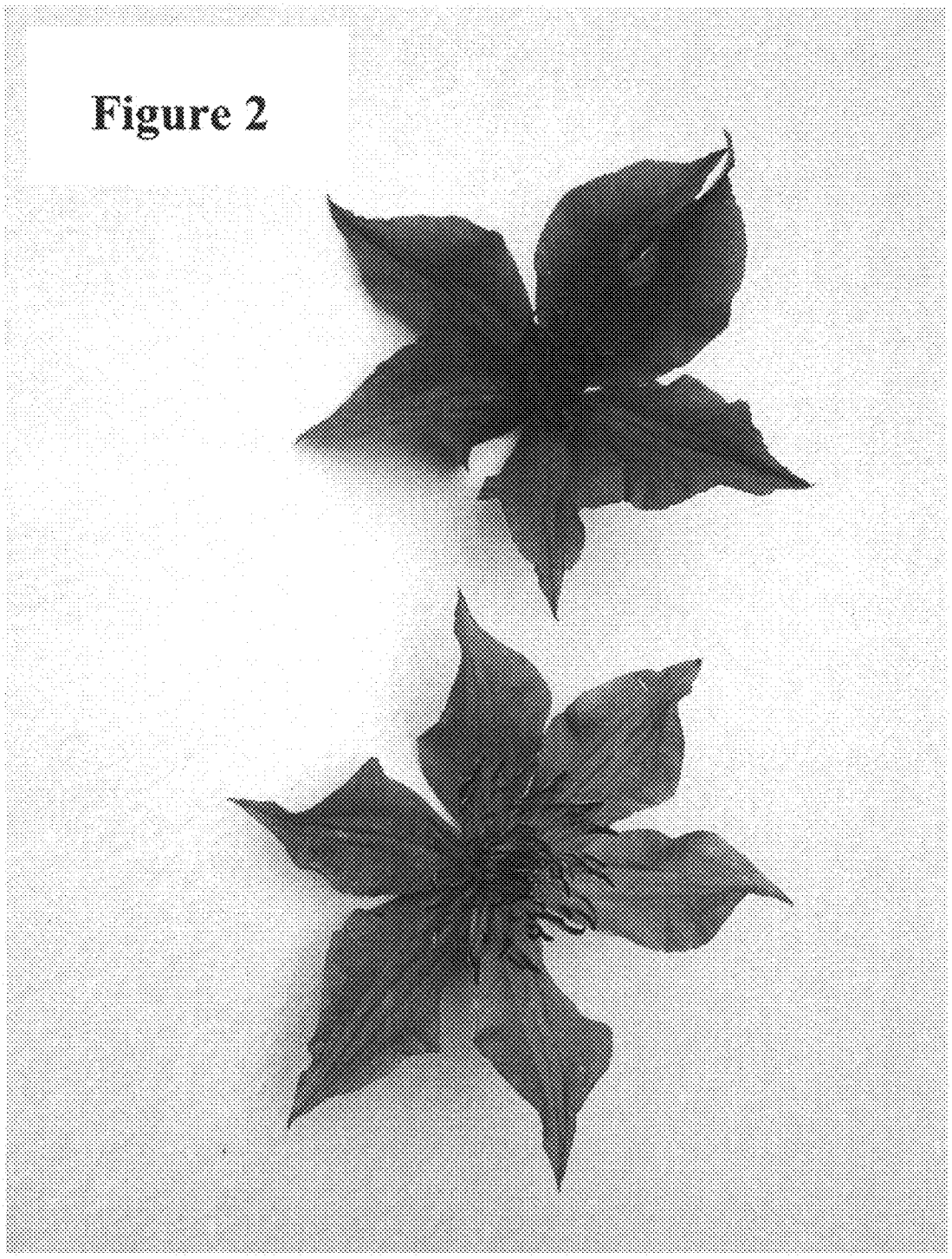
FIG. 2 illustrates a close-up view of flowers at different stages of development.

The following is a detailed description of 'Evipo053', as observed in its growth in Yamhill County, Oreg. Observed plants were cultivated for a period of 24 months in 2 gallon containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo030' described and illustrated in U.S. Plant Pat. No. 15,991 issued Sep. 20, 2005 are compared to 'Evipo053' in Chart 1.

CHART 1

| | 'Evipo053' | 'Evipo030' |
|---|---|---|
| Flower diameter | 70-80 mm | 70-90 mm |
| Tepal upper surface | Violet-Blue Group 90B with light intonations of Purple-Violet N80B | Violet Group N88C |
| Profile | The upper portion is flat, while the lower portion retains a convex profile. | Flat. |

Flower and Flower Bud

Blooming habit: Continuous. The natural flowering period is generally from late May to October.

Flower bud:

*Size.*—Normally 25 mm in length. Bud diameter is 12 mm.

*Bud form.*—Elliptic with a broad base.

*Bud color.*—At ¼ opening, Greyed-Purple N187A, with Greyed-Green Group 191B at the base.

Peduncle:

*Surface texture.*—Smooth, pubescent.

*Length.*—On average 20 mm.

*Color.*—RHS N186A with light intonations of Greyed-Green Group 191B.

*Strength.*—Moderately strong.

Receptacle:

*Surface texture.*—Pubescent.

*Shape.*—Broad funnel.

*Size.*—1 mm (h)×3 mm (w).

*Color.*—RHS N186A.

Flower arrangement:

*Location on vine.*—New and old growth at the terminal bud and directly from axillary buds.

*Borne.*—Singly.

Flower bloom:

*Flower shape.*—Campanulate.

*Size.*—Flowers are 70-80 mm in diameter and 30 mm in depth.

*Profile.*—In viewing an open flower from the side, the upper portion of the whorl of tepals is flat, while the lower portion retains a convex profile.

*Orientation.*—Outwards and upwards.

*Fragrance.*—None.

*Lasting quality.*—Flowers normally remain 15 days on the plant.

*Flower type.*—Single.

Tepals:

*Tepal color.*—Upon opening, the upper surface is Violet-Blue Group 90A with light intonations of Purple-Violet N80A. The lower surface is Violet-Blue Group 90A at the margins. Violet-Blue Group 90C adjacent to margins. A central bar the color of Greyed-Purple Group 183C. After opening, the upper surface is Violet-Blue Group 90B with light intonations of Purple-Violet N80B. The lower surface is Violet Group N88C with intonations of Violet Group 86B at the margins. The underside has a central bar the color of Purple Group N77D.

*Quantity.*—Normally 6 tepals.

*Size.*—40 mm in length by 20 mm wide.

*Shape.*—Individual tepal shape is elliptic. The tepal apex is acuminate. The tepal base is typically acute.

*Apex recurvature.*—None.

*Tepal cross section.*—Slightly cupped.

*Margins.*—Entire. Weak undulations of margin observed.

*Persistence.*—Tepals adhere to the plant.

Reproductive organs:

*Arrangement.*—30 mm in diameter when completely open. 10 mm deep.

*Pollen.*—Quantity: Average. Color: Green-White Group 157D.

*Anthers.*—Size: 5 mm in length. Color: Green-White Group 157D. Quantity: On average, 35.

*Filaments.*—Color: Purple Group N79A to with intonations of Violet Group 84D as the flower ages. Length: 7 mm.

*Pistils.*—Quantity: On average, 15.

*Stigmas.*—Purple-Violet Group N80D.

*Styles.*—Color: Green-White Group 157 D. Length: 10 mm.

Seed head characteristics: None observed.

Plant

Plant form: Spreading.

Plant growth: Moderately vigorous.

Size: Seasons growth attains approximately 70 cm in height. Average spread is 70 cm.

Stems:

*Color.*—Juvenile stems are Yellow-Green Group 144C. Mature stems are Brown Group 200A.

*Internodes.*—On average, 45 mm between nodes.

*Length.*—Normally 20 cm from the base of the plant to the flowering portion of the stem.

*Diameter.*—Normally 2 mm.

*Texture.*—Mature stems are smooth and ribbed.

Plant foliage:

*Leaf characteristics.*—Deciduous.

*Arrangement.*—Simple, opposite.

*Leaf size.*—Leaflets are normally 50 mm from the base to apex, and 30 mm wide.

Abundance: On average 6 leaves per 10 cm of stem.

*Leaf color.*—Juvenile upper Yellow-Green Group 146A. Juvenile lower Yellow-Green Group 146B. Mature upper Yellow-Green Group 146A. Mature lower Yellow-Green Group 146B.

*Stipules.*—Absent.

*Petioles.*—Size: Normally 25 mm in length by 2 mm diameter. Texture: Smooth and pubescent. Color: Yellow-Green Group 146B.

*Leaflet shape.*—Generally lanceolate. The base is rounded. The apex is acute.

*Margin.*—Leaves with entire margin, as well as tri-lobed occur on the plant.

*Surface*.—The upper side is smooth and somewhat glossy. The lower side is smooth and somewhat glossy.

*Thickness*.—Average.

Disease resistance: Subject to any disease that normally attacks the species. However the variety is more tolerant to *clematis* wilt than some *clematis*.

Cold hardiness: The variety is tolerant to USDA Hardiness Zone 6.

Heat tolerance: The variety has been found to be suitable for climate conditions found in The American Horticulture Society heat zone 7.

We claim:

1. A new and distinct variety of *clematis* plant named 'Evipo053', substantially as described and illustrated herein, due to its abundant Violet-Blue flowers with good keepability, attractive foliage, compact growth, suitability for production from softwood cuttings in pots, which make the variety suitable for distribution in the floral industry.

* * * * *